US012690854B2

(12) United States Patent
Abraham et al.

(10) Patent No.: US 12,690,854 B2
(45) Date of Patent: Jul. 28, 2026

(54) OPHTHALMIC SPECULUM WITH AN AIR-FLOW SYSTEM

(71) Applicant: Alcon Inc., Fribourg (CH)

(72) Inventors: Mario Abraham, Burgthann (DE); Michael Wittnebel, Hirschaid (DE)

(73) Assignee: Alcon Inc., Fribourg (CH)

( * ) Notice: Subject to any disclaimer, the term of this patent is extended or adjusted under 35 U.S.C. 154(b) by 256 days.

(21) Appl. No.: 18/406,931

(22) Filed: Jan. 8, 2024

(65) Prior Publication Data

US 2024/0138827 A1 May 2, 2024

Related U.S. Application Data

(63) Continuation of application No. 17/655,056, filed on Mar. 16, 2022, now Pat. No. 11,896,209.

(60) Provisional application No. 63/164,615, filed on Mar. 23, 2021.

(51) Int. Cl.
*A61B 17/02* (2006.01)
*A61F 9/008* (2006.01)

(52) U.S. Cl.
CPC .... *A61B 17/0231* (2013.01); *A61B 2218/005* (2013.01); *A61B 2218/006* (2013.01); *A61F 9/00804* (2013.01)

(58) Field of Classification Search
CPC .......... A61B 17/0231; A61B 2218/005; A61B 2218/006; A61F 9/00804; A61F 9/008–009; A61F 2002/00872
USPC .................. 600/201, 205, 208, 236; 606/4–6
See application file for complete search history.

(56) References Cited

U.S. PATENT DOCUMENTS

| | | | | |
|---|---|---|---|---|
| 5,070,860 A | * | 12/1991 | Grounauer | A61B 17/0231 |
| | | | | 600/236 |
| 5,971,977 A | * | 10/1999 | Korenfeld | A61F 9/008 |
| | | | | 606/4 |
| 2002/0065510 A1 | * | 5/2002 | Guimaraes | A61F 9/00804 |
| | | | | 606/5 |
| 2003/0171656 A1 | * | 9/2003 | Foulkes | A61B 17/0231 |
| | | | | 600/232 |
| 2004/0147944 A1 | * | 7/2004 | LaHaye | A61F 9/009 |
| | | | | 606/4 |
| 2017/0239087 A1 | * | 8/2017 | Sahler | A61F 9/009 |
| 2019/0298330 A1 | * | 10/2019 | Martinez | A61B 1/32 |
| 2022/0096272 A1 | * | 3/2022 | Abraham | A61F 9/0008 |

FOREIGN PATENT DOCUMENTS

| | | |
|---|---|---|
| CN | 1307458 A | 8/2001 |
| CN | 203943799 U | 11/2014 |
| CN | 209091464 U | 7/2019 |

(Continued)

*Primary Examiner* — Eduardo C Robert
*Assistant Examiner* — David C Comstock

(57) ABSTRACT

An ophthalmic speculum includes arms, a locking mechanism, and an air-flow system. The arms include a first arm and a second arm. Each arm has a retractor shaped to conform to an eyelid of a pair of eyelids of an eye. The retractors are substantially symmetrical about a lateral axis. The locking mechanism is coupled to the arms. The locking mechanism moves the arms to allow the retractors to retract the pair of eyelids, and fixes the arms into place to maintain retraction of the pair of eyelids. The air-flow system is coupled to at least one arm, and moves air in a region disposed outwardly from a surface of the eye.

18 Claims, 6 Drawing Sheets

(56) References Cited

FOREIGN PATENT DOCUMENTS

| JP | 2005504565 A | 2/2005 |
| JP | 2014036814 A | 2/2014 |
| JP | 2020124330 A | 8/2020 |
| WO | 9966843 A1 | 12/1999 |
| WO | 03002010 A1 | 1/2003 |

* cited by examiner

OPHTHALMIC SPECULUM WITH AN AIR-FLOW SYSTEM

PRIORITY CLAIM

This application is a continuation of U.S. Non-Provisional patent application Ser. No. 17/655,056 filed Mar. 16, 2022, which claims the benefit of priority of U.S. Provisional Patent Application Ser. No. 63/164,615 titled "OPHTHAL-MIC SPECULUM WITH AN AIR-FLOW SYSTEM," filed on Mar. 23, 2021, whose inventors are Mario Abraham and Michael Wittnebel, both of which are hereby incorporated by reference in their entirety as though fully and completely set forth herein.

TECHNICAL FIELD

The present disclosure relates generally to ophthalmic devices, and more particularly to an ophthalmic speculum with an air-flow system.

BACKGROUND

Laser ablation removes material from a surface by irra-diating it with a laser beam. In ophthalmic surgery, an excimer laser can be used to ablate and reshape the cornea to change its refractive properties. There are different types of refractive surgery techniques. Laser in-situ keratomileusis (LASIK) involves cutting a flap in the cornea and then using the laser to ablate the stroma. Photo refractive keratectomy (PRK) is similar to LASIK, except that instead of creating a flap, the surface cells of the cornea are removed and then allowed to grow back after surgery.

During laser ablation, ablation products (e.g., tissue par-ticles) often form an unwanted mist above the area of ablation. Such ablation products enter into the laser beam path, where they undesirably attenuate the intensity of the laser beam.

BRIEF SUMMARY

In certain embodiments, an ophthalmic speculum includes arms, a locking mechanism, and an air-flow system. The arms include a first arm and a second arm. Each arm has a retractor shaped to conform to an eyelid of a pair of eyelids of an eye. The retractors are substantially symmetrical about a lateral axis. The locking mechanism is coupled to the arms. The locking mechanism moves the arms to allow the retrac-tors to retract the pair of eyelids, and fixes the arms into place to maintain retraction of the pair of eyelids. The air-flow system is coupled to at least one arm, and moves air in a region disposed outwardly from a surface of the eye.

Embodiments may include none, one, some, or all of the following features: The air-flow system moves the air as a laminar flow across the surface of the eye in a direction orthogonal to the lateral axis. An aspirator may move the air away from the surface of the eye, and/or an air blower may move the air across the surface of the eye. The air-flow system creates a low-pressure area that moves the air towards the surface of the eye and then away from the surface of the eye. The air-flow system may include one or more aspirators, where each aspirator moves the air away from the surface of the eye towards a retractor of the plurality of retractors.

The air-flow system creates a rotational flow of air that moves the air away from the surface of the eye. The air-flow system may include: an aspirator configured to move the air away from the surface of the eye towards a first retractor of the plurality of retractors; and an air blower configured to move the air across the surface of the eye away from a second retractor of the plurality of retractors. The air-flow system may include: a first air blower configured to move the air across the surface of the eye away from a first retractor of the plurality of retractors; and a second air blower configured to move the air across the surface of the eye away from a second retractor of the plurality of retrac-tors. The air-flow system may include: a first aspirator configured to move the air away from the surface of the eye towards a first retractor of the plurality of retractors; and a second aspirator configured to move the air away from the surface of the eye towards a second retractor of the plurality of retractors.

In certain embodiments, a method for moving air away from an eye includes moving a plurality of arms to allow retractors to retract a pair of eyelids. The arms includes a first arm and a second arm, where each arm has a retractor shaped to conform to an eyelid. The retractors are substan-tially symmetrical about a lateral axis. The method further includes: fixing, by a locking mechanism, the arms into place to maintain a retraction of the pair of eyelids; and moving, by an air-flow system coupled to at least one arm, air in a region disposed outwardly from a surface of the eye.

Embodiments may include none, one, some, or all of the following features: The method includes controlling, by a computer, the air-flow system to move the air. The air-flow system moves the air as a laminar flow across the surface of the eye in a direction orthogonal to the lateral axis. The air-flow system creates a low-pressure area that moves the air towards the surface of the eye and then away from the surface of the eye. The air-flow system creates a rotational flow of air that moves the air away from the surface of the eye.

In certain embodiments, an ophthalmic speculum includes arms, a locking mechanism, an air-flow system, and a computer. The arms include a first arm and a second arm. Each arm has a retractor shaped to conform to an eyelid of a pair of eyelids of an eye. The retractors are substantially symmetrical about a lateral axis. The locking mechanism is coupled to the arms. The locking mechanism moves the arms to allow the retractors to retract the pair of eyelids, and fixes the arms into place to maintain retraction of the pair of eyelids. The air-flow system is coupled to at least one arm, and moves air in a region disposed outwardly from a surface of the eye. The air-flow system includes: one or more aspirators, where each aspirator moves the air away from the surface of the eye; and one or more air blowers, where each air blower moves the air across the surface of the eye. The computer can control the air-flow system to: move the air as a laminar flow across the surface of the eye in a direction orthogonal to the lateral axis; create a low-pressure area that moves the air towards the surface of the eye and then away from the surface of the eye; and create a rotational flow of air that moves the air away from the surface of the eye.

Embodiments may include none, one, some, or all of the following features: The one or more aspirators include: a first aspirator configured to move the air away from the surface of the eye towards a first retractor of the plurality of retractors; and a second aspirator configured to move the air away from the surface of the eye towards a second retractor of the plurality of retractors. The one or more air blowers include: a first air blower configured to move the air across the surface of the eye away from a first retractor of the plurality of retractors; and a second air blower configured to move the air across the surface of the eye away from a second retractor of the plurality of retractors.

DESCRIPTION OF EXAMPLE EMBODIMENTS

Figure 1:
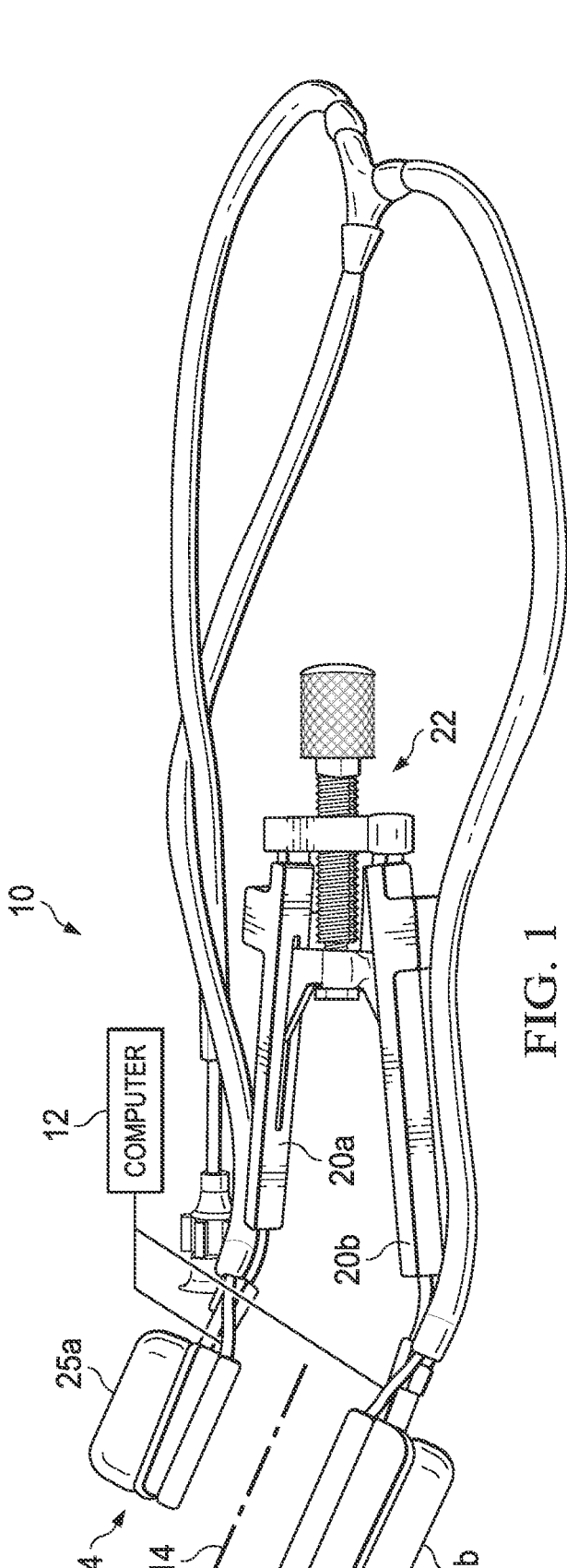
FIG. 1 illustrates an example of an ophthalmic speculum according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

During laser ablation, ablation products (e.g., tissue particles) often form an unwanted mist above the area of ablation. The ablation products enter into the laser beam path, where they undesirably attenuate the intensity of the laser beam. Certain embodiments may address this problem.

FIG. 1 illustrates an example of an ophthalmic speculum 10 according to certain embodiments. In the example, ophthalmic speculum 10 includes arms 20 (20a, 20b), a locking mechanism 22, and an air-flow system 24, coupled as shown. Each arm 20 has a retractor 25 (25a, 25b) that is shaped to conform to an eyelid of the eyelids of an eye. Locking mechanism 22 moves arms 20 to allow retractors 25 to retract the eyelids and then fixes arms 20 into place to maintain the retraction. Air-flow system 24 comprises one or more air-flow devices that move the air disposed outwardly from the surface of the eye. The air movement moves the ablation products away from the eye to reduce unwanted attenuation of the laser beam. In certain embodiments, a computer 12 may instruct air-flow system 24 to move the air.

Turning to the parts of the example, ophthalmic speculum 10 has arms 20 with a retractor 25 (25a, 25b). Arms 20 and retractors 25 comprise a material sufficiently strong to retract eyelids, e.g., metal or plastic. A retractor 25 is sized and shaped to conform to an eyelid, and retractors 25 may be substantially symmetrical about a lateral axis 14. Retractor 25 may have a curved or hooked shape in a direction substantially orthogonal to lateral axis 14, where the curved or hooked shape engages the eyelid to move the eyelid away from the eye. Retractor 25 may have a straight or curved shape in a direction substantially parallel to lateral axis 14. In the illustrated example, retractor 24 has a curved shape in the direction substantially orthogonal to lateral axis 14 and a straight shape direction substantially parallel to lateral axis 14. Locking mechanism 22 comprises any suitable parts to move arms 20 and fix arms 20 into place, e.g., screws or springs.

Air-flow system 24 comprises one or more air-flow devices that move air disposed outwardly from the surface of the eye. An air-flow device is a device that moves air in any suitable direction. For example, an air blower (e.g., a fan) generally moves air away from itself, and an aspirator generally moves air towards itself. In certain embodiments, an air blower moves (or blows) air across the surface of an eye, and an aspirator moves (or aspirates) air away from the surface.

An air-flow device may use any suitable technology to move air. For example, an air-flow device may use a traditional fan to move air. A traditional fan may be an apparatus with rotating blades that create a current of air. As another example, a Dyson bladeless fan with a base and loop may be used. The base may have an impeller (e.g., a mixed flow impeller) with fins (asymmetric or symmetric) that draw air into the fan. As the impeller builds up air pressure, the air is forced into and through the loop. The airflow through the loop creates a low-pressure area, which induces surrounding air to follow the airflow via entrainment.

As another example, an air-flow device may move air with technology based on the Venturi effect. Examples of such Venturi air-flow devices include an air ejector, Venturi pump, and vacuum ejector. In a Venturi air-flow device, a working fluid flows through a tube that first narrows and then expands in cross-sectional area. The fluid exits at a high velocity, resulting in a low-pressure area, which generates a vacuum. In certain cases, an outer tube narrows into a mixing section where the high velocity working fluid mixes with another fluid drawn in by the vacuum, imparting enough velocity for the fluids to be ejected. Other suitable technologies may be used, e.g., air-flow devices that move air using jet engine technology or that move air with differences in temperature and/or humidity.

Air-flow system 24 may move air to create any suitable air-flow pattern. An air-flow pattern describes a relatively consistent movement of air. Examples of air-flow patterns include a laminar flow across an eye (laminar pattern), a flow away from the eye that creates a low-pressure region at the eye (low-pressure pattern), and a rotational flow that moves air away from the eye (rotational pattern).

In certain embodiments, computer 12 may control air-flow system 24 to move air. In the embodiments, computer may control how an air-flow device (e.g., an air blower or an aspirator) moves air to create an air-flow pattern. For example, computer may send instructions to a device about when to move air, how much air to move, and/or how fast to move air to create the air-flow pattern.

Figure 2A:
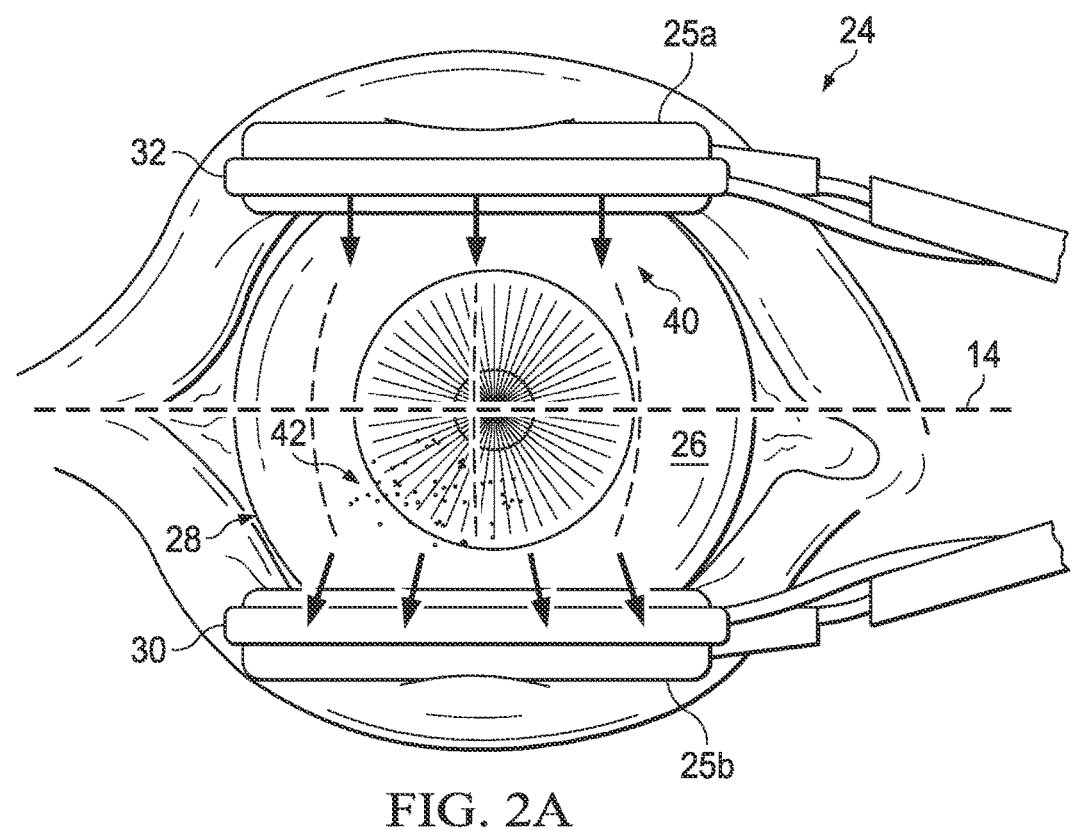
FIGS. 2A, 2B, and 2C illustrate an example of an air-flow system that moves air as a laminar flow that may be used with the ophthalmic speculum of FIG. 1.
Figure 2B:
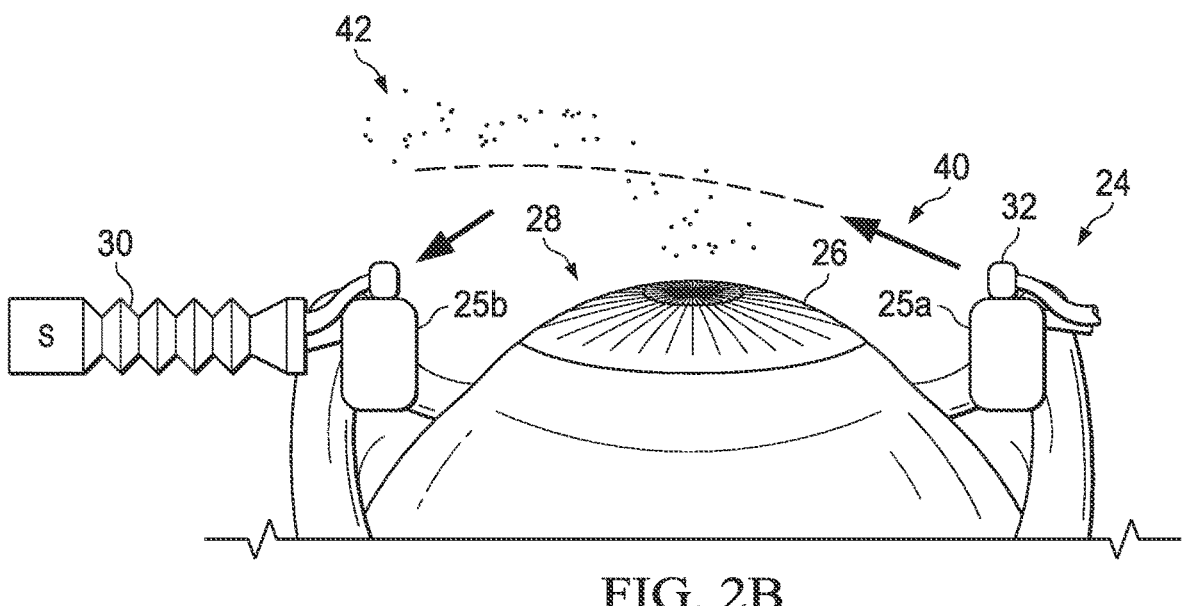
Figure 2C:
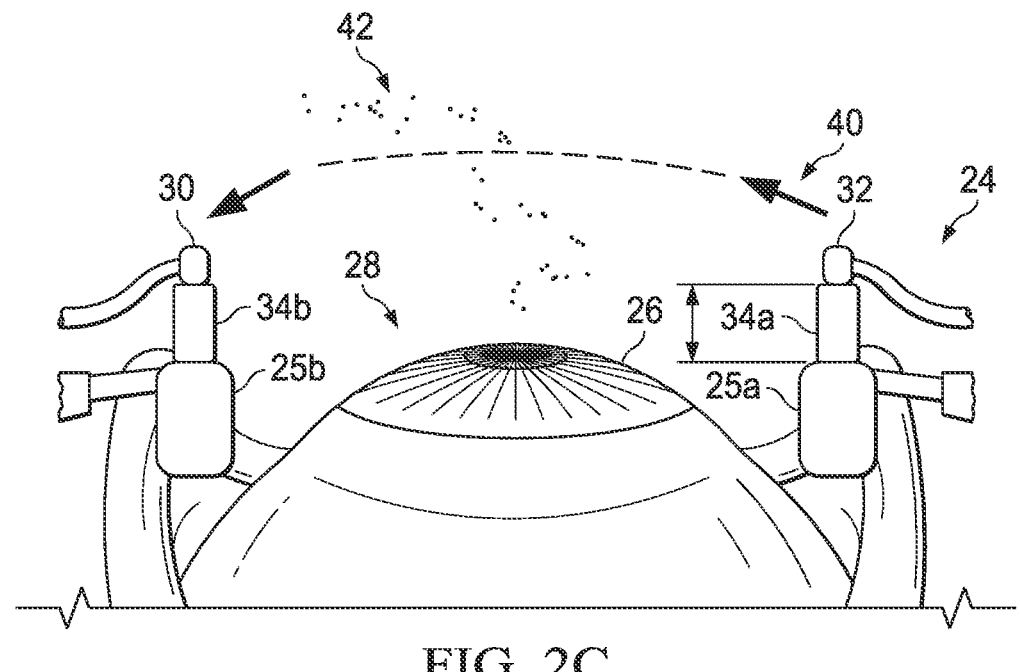

FIGS. 2A to 2C illustrate an example of air-flow system 24 that moves air as a laminar flow 40 of a laminar pattern that may be used with ophthalmic speculum 10 of FIG. 1. Laminar flow 40 moves across the surface 26 of an eye 28 in a direction substantially orthogonal to the lateral axis 14. FIG. 2A is a top view of air-flow system 24, and FIG. 2B is a side view of air-flow system 24.

In the illustrated example, air-flow system 24 includes an air blower 32 coupled to retractor 25a and/or an aspirator 30 coupled to retractor 25b. Air blower 32 blows air across surface 26 of eye 28 away from retractor 25a. Aspirator 30 aspirates air away from surface 26 of eye 28 towards retractor 25b. As air blower 32 blows air and aspirator 30 aspirates air, laminar flow 40 across surface 26 of eye 28 and orthogonal to lateral axis 14 moves aspiration products 42 away from eye 28. In other examples, laminar flow 40 may be at an angle other than orthogonal to lateral axis 14, e.g., an angle in the range of 40 to 90 degrees, such as an angle in the range of 40 to 50, 50 to 70, and/or 70 to 90 degrees.

FIG. 2C is a side view of air-flow system 24 that includes spacers 34 (34a, 34b). Spacers 34 can be used to adjust the distance between air blower 32 and aspirator 30 and surface 26 of eye 28, which changes the distance between laminar flow 40 and surface 26. The distance between laminar flow 40 and surface 26 may be increased to reduce the drying effect of laminar flow 40 on eye 28.

Figure 3A:
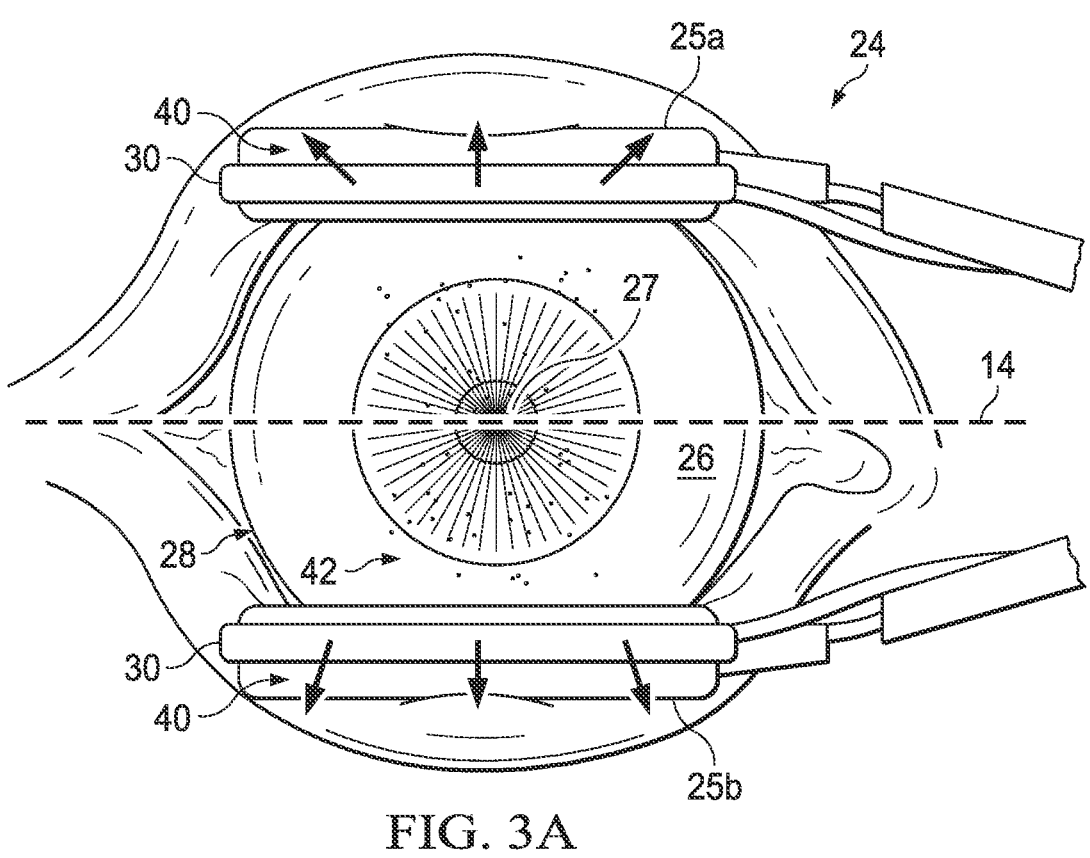
FIGS. 3A and 3B illustrate an example of an air-flow system that creates a low-pressure area that may be used with the ophthalmic speculum of FIG. 1.
Figure 3B:
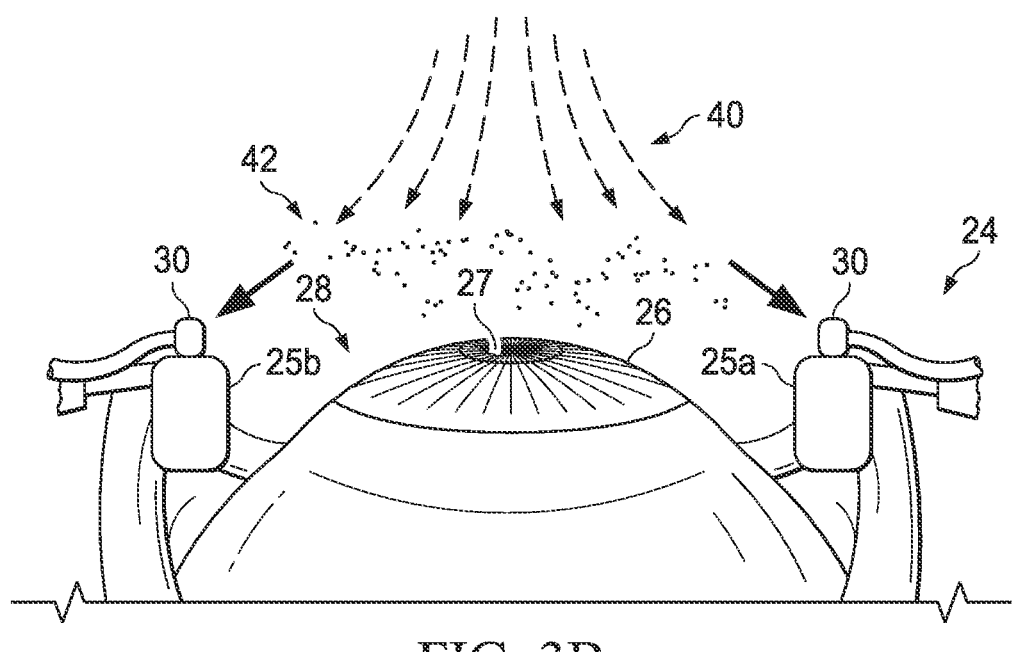

FIGS. 3A and 3B illustrate an example of air-flow system 24 that creates a low-pressure area 50 of a low-pressure pattern that may be used with ophthalmic speculum 10 of FIG. 1. In the example, air-flow system 24 moves air 40 and ablation products 42 towards surface 26 of eye 28 and then away from the center 27 of eye 28. FIG. 3A is a top view of air-flow system 24, and FIG. 3B is a side view of air-flow system 24.

In the illustrated example, air-flow system 24 includes one or two aspirators 30 coupled to retractors 25. Each aspirator 30 aspirates air away from surface 26 of eye 28 towards its associated retractor 25. In certain embodiments, only one retractor 25 has an associated aspirator 30. In other embodiments, both retractors 25 have an associated aspirator 30. In these embodiments, a first aspirator aspirates air away from surface 26 of eye 28 towards a first retractor, and a second aspirator aspirates air away from surface 26 of eye 28 towards a second retractor. The resulting movement of air creates a low-pressure area 50 that moves air 40 towards surface 26 of eye 28, and then air-flow devices move air 40 away from center 27 of eye 28.

Figure 4A:
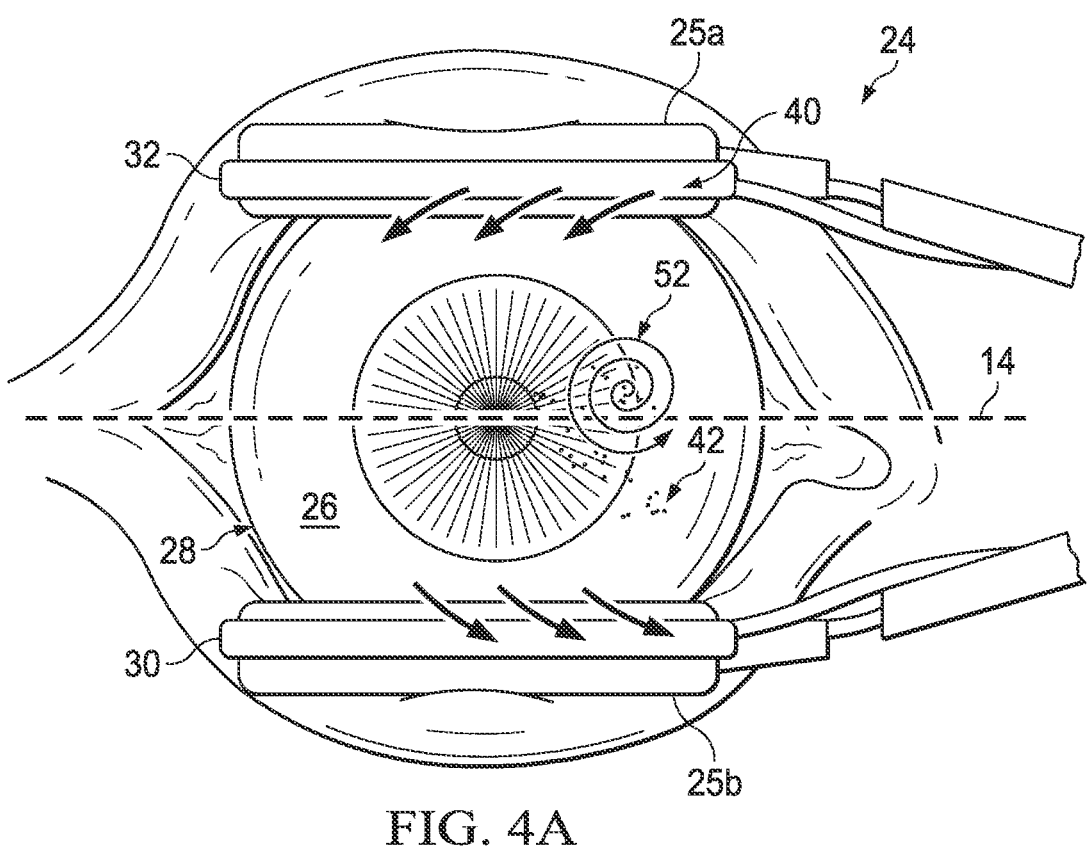
FIGS. 4A, 4B, and 4C illustrate an example of an air-flow system that creates a rotational air movement that may be used with the ophthalmic speculum of FIG. 1.
Figure 4B:
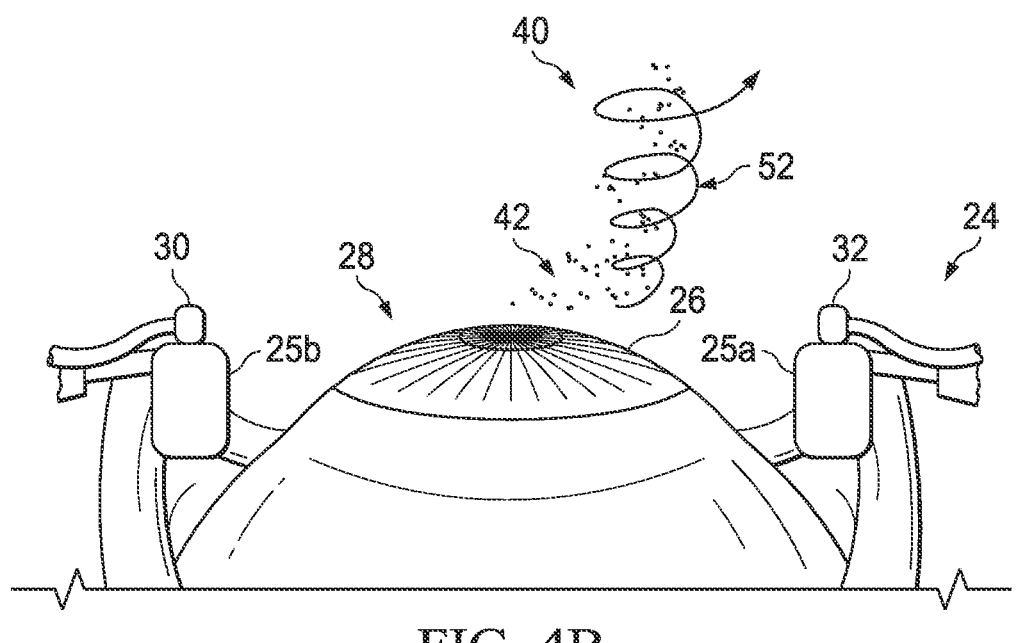
Figure 4C:
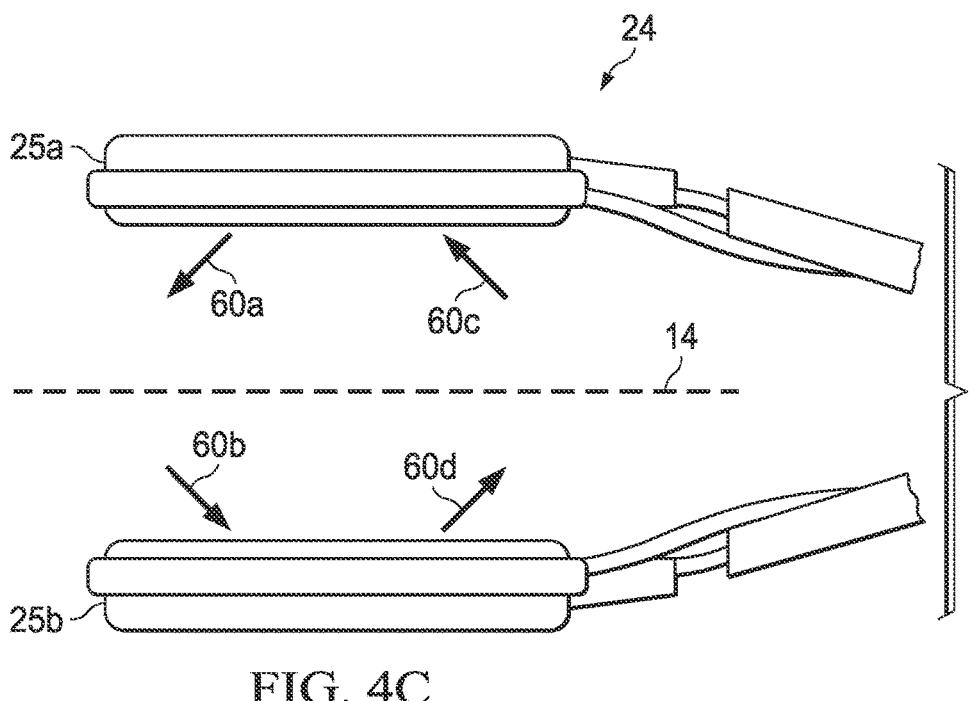

FIGS. 4A to 4C illustrate an example of air-flow system 24 that creates rotational air movement 52 of a rotational pattern that may be used with ophthalmic speculum 10 of FIG. 1. Rotational air movement 52 moves air 40 and ablation products 42 away from surface 26 of eye 28. FIG. 4A is a top view of air-flow system 24, and FIG. 4B is a side view of air-flow system 24. FIG. 4C illustrates examples of rotational flow angles 60 (60a-d).

Turning to FIG. 4C, a rotational flow angle 60 is an angle of air flow that can create rotational air movement 52. In the illustrated example, air flow at two or more angles 60 may create rotational air movement 52. Generally, a rotational flow angle 60 is not parallel to or perpendicular to lateral axis 14. Examples of a rotational flow angle 60 may have a value in the range of 10 to 80 degrees (e.g., a value in a range of 10 to 35, 35 to 55, and/or 55 to 80 degrees) with respect to lateral axis 14. An air blower may move (e.g., blow) air at an angle 60a, 60d, and an aspirator may move (e.g., aspirate) air at an angle 60b, 60c.

Turning to FIGS. 4A and 4B, in certain embodiments, air-flow system 24 includes one or more air-flow devices (e.g., air blower 32 and/or aspirator 30) that move air 40 in a rotational direction. Any suitable combination of air-flow devices that creates a rotational movement of air at eye 28 may be used. In the illustrated example, air-flow system 24 includes air blower 32 coupled to retractor 25a and aspirator 30 coupled to retractor 25b. Air blower 32 blows air across surface 26 of eye 28 away from retractor 25a at rotational flow angle 60a. Aspirator 30 aspirates air away from surface 26 of eye 28 towards retractor 25b at a rotational flow angle 60b.

Other suitable combinations of air-flow devices that create a rotational movement of air at eye 28 may be used. For example, air-flow system 24 may include a first air blower 32 coupled to retractor 25a, and a second air blower 32 coupled to retractor 25b. First air blower 32 moves air across surface 26 of eye 28 away from retractor 25a at rotational flow angle 60a, and second air blower 32 moves air across surface 26 of eye 28 away from second retractor 25b at rotational flow angle 60d.

As another example, air-flow system 24 may include a first aspirator 30 coupled to retractor 25a, and a second aspirator 30 coupled to retractor 25b. First aspirator 30 moves air away from surface 26 of eye 28 towards retractor 25a at rotational flow angle 60c, and second aspirator 30 moves air away from surface 26 of eye 28 towards retractor 25b at rotational flow angle 60b.

Figure 5:
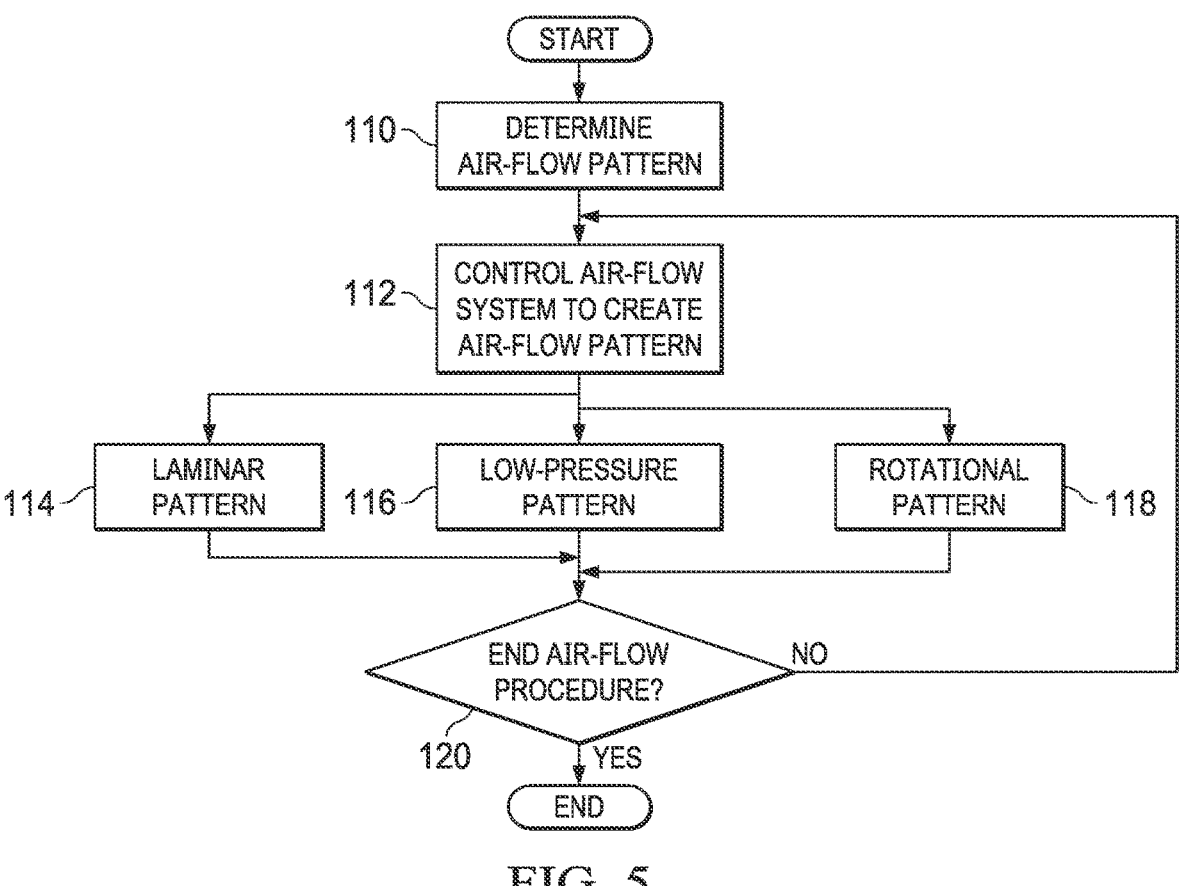
FIG. 5 illustrates an example of an air-flow method that may be used with the ophthalmic speculum of FIG. 1.

FIG. 5 illustrates an example of an air-flow method that may be used with the ophthalmic speculum of FIG. 1. In certain embodiments, computer 12 may perform the method, and the method may be performed to remove ablation products during an ophthalmic procedure.

The method starts at step 110, where computer 12 determines the air-flow pattern. The air-flow pattern may be, e.g., a laminar, low-pressure, rotational of other suitable pattern. In certain embodiments, computer 12 may determine the pattern from, e.g., user input or a predetermined setting. For example, certain patterns may be selected for certain procedures.

Computer 12 controls air-flow system 24 at step 112 to create the air-flow pattern. The next step depends on the determined air-flow pattern. For a laminar pattern, the method proceeds to step 114 to create a laminar pattern. An example of creating a laminar pattern is described with reference to FIGS. 2A to 2C. For a low-pressure pattern, the method proceeds to step 116 to create a low-pressure pattern. An example of creating a low-pressure pattern is described with reference to FIGS. 3A and 3B. For a rotational pattern, the method proceeds to step 114 to create a rotational pattern. An example of creating a rotational pattern is described with reference to FIGS. 4A to 4C.

The air-flow procedure may end at step 120. For example, an ablation process of the ophthalmic procedure may be ending, and thus there may no longer be a need for removal of ablation products. If the air-flow procedure is not to end, the method returns to step 112, to continue to control air-flow system 24 to create the air-flow pattern. If the air-flow procedure is to end, the method ends.

A component (such as computer 12) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic speculum comprising:
   a plurality of arms comprising a first arm and a second arm, each arm having a retractor shaped to conform to an eyelid of a pair of eyelids of an eye;
   a locking mechanism coupled to the arms and configured to:
      move the arms to allow the retractors to retract the pair of eyelids; and
      fix the arms into place to maintain retraction of the pair of eyelids; and
   an air-flow system coupled to at least one a of the plurality of arms, the air-flow system configured to move air in a region disposed outwardly from a surface of the eye in a laminar flow across a surface of the eye, wherein the laminar flow is generally in a direction from a first eyelid to a second eyelid of the pair of eyelids.

2. The ophthalmic speculum of claim 1, wherein a height of the laminar flow relative to the surface of the eye is adjustable.

3. The ophthalmic speculum of claim 2, further comprising spacers between the at least one arm and the air-flow system to raise the height of the laminar flow relative to the surface of the eye.

4. The ophthalmic speculum of claim 1, the air-flow system comprising:
   an aspirator configured to move the air away from the surface of the eye.

5. The ophthalmic speculum of claim 4, the aspirator coupled to the second arm proximate the second eyelid.

6. The ophthalmic speculum of claim 1, the air-flow system comprising:
   an air blower configured to move the air across the surface of the eye.

7. The ophthalmic speculum of claim 6, the air blower coupled to the first arm proximate the first eyelid.

8. The ophthalmic speculum of claim 1, the air-flow system comprising:
   an aspirator configured to move the air away from the surface of the eye; and
   an air blower configured to move the air across the surface of the eye.

9. The ophthalmic speculum of claim 8, the air blower coupled to the first arm proximate the first eyelid and the aspirator coupled to the second arm proximate the second eyelid.

10. The ophthalmic speculum of claim 1, wherein the air-flow system is further configured to move the air as a rotational flow away from the surface of the eye, and is switchable between the laminar flow and the rotational flow.

11. The ophthalmic speculum of claim 1, wherein the air-flow system is further configured to create a low-pressure area that moves the air towards the surface of the eye and then away from the surface of the eye, the air-flow system switchable between the laminar flow and the low-pressure area creation.

12. A method for moving air away from a surface of an eye, comprising:
   moving a plurality of arms to allow a plurality of retractors to retract a pair of eyelids, the plurality of arms comprising a first arm and a second arm, each arm having a retractor of the plurality of retractors, the retractor shaped to conform to an eyelid of the pair of eyelids of the eye;
   fixing, by a locking mechanism, the arms into place to maintain retraction of the pair of eyelids; and
   moving, by an air-flow system coupled to at least one arm, air in a region disposed outwardly from the surface of the eye, the air moved in a laminar flow that moves the air across the surface of the eye, wherein the laminar flow is generally in a direction from a first eyelid to a second eyelid of the pair of eyelids.

13. The method of claim 12, further comprising:
   controlling, by a computer, the air-flow system to move the air.

14. The method of claim 13, wherein the computer is configured to change the airflow system from the laminar flow of air into a rotational air flow that moves the air outwardly away from the surface of the eye.

15. The method of claim 13, wherein the computer is configured to change the airflow system from the laminar flow of air into a low-pressure creation air flow that moves the air away from the surface of the eye.

16. An ophthalmic speculum comprising:
   a plurality of arms comprising a first arm and a second arm, each arm having a retractor shaped to conform to an eyelid of a pair of eyelids of an eye;
   a locking mechanism coupled to the arms and configured to:
      move the arms to allow the retractors to retract the pair of eyelids; and
      fix the arms into place to maintain retraction of the pair of eyelids;
   an air-flow system coupled to at least one arm of the plurality of arms, the air-flow system configured to move air in a region disposed outwardly from a surface of the eye, the air-flow system comprising:
      one or more aspirators, each aspirator configured to move the air away from the surface of the eye; and
      one or more air blowers, each air blower configured to move the air across the surface of the eye; and a computer configured to:
   determine an air-flow pattern; and
   control the air-flow system to create the determined
      air-flow pattern, the airflow patterns comprising at
      least one of:
      a laminar flow across the surface of the eye;
      a low-pressure area that moves the air towards the
         surface of the eye and then away from the surface
         of the eye; and
      a rotational flow of air that moves the air away from
         the surface of the eye.

17. The ophthalmic speculum of claim 16, the one or more
aspirators comprising:
   a first aspirator configured to move the air away from the
      surface of the eye towards a first retractor of the
      retractors; and
   a second aspirator configured to move the air away from
      the surface of the eye towards a second retractor of the
      retractors.

18. The ophthalmic speculum of claim 16, the one or more
air blowers comprising:
   a first air blower configured to move the air across the
      surface of the eye away from a first retractor of the
      retractors; and
   a second air blower configured to move the air across the
      surface of the eye away from a second retractor of the
      retractors.

* * * * *